United States Patent [19]

Schraufstatter et al.

[11] Patent Number: 5,831,032

[45] Date of Patent: Nov. 3, 1998

[54] INTERLEUKIN-8 ANTI-PEPTIDE ANTIBODIES

[75] Inventors: Ingrid U. Schraufstatter, San Diego; Charles G. Cochrane, La Jolla, both of Calif.

[73] Assignee: The Scripps Research Institute, La Jolla, Calif.

[21] Appl. No.: 643,515

[22] Filed: May 6, 1996

Related U.S. Application Data

[62] Division of Ser. No. 342,348, Nov. 21, 1994, abandoned, which is a continuation of Ser. No. 755,824, Sep. 6, 1991, abandoned, which is a continuation-in-part of Ser. No. 581,673, Sep. 12, 1990, abandoned.

[51] Int. Cl.⁶ .................................................. C07K 16/24
[52] U.S. Cl. ..................................... 530/387.9; 530/388.1; 530/388.23; 530/389.2; 530/326; 530/412; 530/413
[58] Field of Search .............................. 560/387.1, 388.1, 560/388.25, 389.2, 387.9, 326; 514/412, 413

[56] References Cited

PUBLICATIONS

Van Damme et al. (1989) Eur. J. Immunol. vol. 19. pp. 1189–1194.
Strieter et al. (1989) J. Biol. Chem. vol. 264, No. 18, pp. 10621–10626.
Thornton et al. (1990) J. Immunol. vol. 144, No. 7, pp. 2609–2613.
Wang et al. (1990) Biochem. Biophys Res Comm. vol. 169, No. 1, pp. 165–170.
Matsushima et al. (1990) Immunology vol. 69, pp. 548–553.
Serrer et al. (1981) Clin. Chem vol. 27, No. 11, pp. 1797–1806.

*Primary Examiner*—Stephen Walsh
*Assistant Examiner*—Prema Mertz
*Attorney, Agent, or Firm*—Thomas Fitting; Emily Holmes

[57] ABSTRACT

Polypeptide analogs, antibodies, diagnostic and therapeutic compositions as well as methods for detecting the presence of IL-8 and preventing the inflammatory response in patients are described.

6 Claims, 3 Drawing Sheets

INTERLEUKIN-8 ANTI-PEPTIDE ANTIBODIES

CROSS REFERENCE TO RELATED APPLICATION

This is a division of application Ser. No. 08/342,648 filed Nov. 21, 1994, now abandoned, which is a continuation of copending application Ser. No. 07/755,824, filed Sep. 6, 1991, now abandoned, which is a continuation-in-part application of copending application Ser. No. 07/581,673 filed Sep. 12, 1990, now abandoned, the disclosures of which are hereby incorporated by reference.

This application describes inventions made with support of the Government of the Unites States of America, and therefore the Government may have certain rights in the invention pursuant to research support under National Institutes of Health grant number HL23584.

TECHNICAL FIELD

The present invention relates to cytokines and their role in inflammatory reactions. More specifically, this invention relates to a polypeptide analog of IL-8 active site, antibodies to the active site, and methods suitable for inhibiting inflammation by neutralizing the receptor-interacting site of IL-8.

BACKGROUND ART

Immunocompetent cells and vascular endothelium interact in producing hemostasis as well as inflammatory and immune reactions. Mediators of these intricate bidirectional interactions between leukocytes and vascular cells are the cytokines, which are produced by and act on endothelial cells (*Immunol. Today*, 10:370–375 (1989). Cytokines effect their influence on endothelial cells causing them to release chemoattractants that induce chemotaxis and extravasation of polymorphonuclear cells and monocytes [Broudy et al., *J. Immunol.*, 139:464–468 (1987); Sieff et al., *Blood*, 72:1316–1323 (1988)]. This recruitment and activation of leukocytes severely disrupts the architecture of vessel walls and underlying tissues, causing injury.

Belonging to a growing family of monomeric peptide cytokines induced by lipopolysaccharides (LPS), tumor necrosis factor (TNF) or other cytokines, IL-8 is a putative mediator of tissue injury in septic shock, acute respiratory distress syndrome (ARDS), and generally during inflammatory disease or conditions associated with increased TNF production. IL-8 has recently been detected in bronchoalveolar lavage fluid of patients with early ARDS.

Nomenclature for the new group of cytokines comprising IL-8 has not been established. Intact IL-8 appears to be identical to monocyte-derived neutrophil chemotactic factor (MDNCF) [Matsushima et al., *J. Exp. Med.*, 167:1883–1893 (1988)], neutrophil activating factor (NAF) [Lindley et al., *Proc. Natl. Acad. Sci. USA*, 85:9199–9203 (1988); PCT No. WO 89/04836] and neutrophil chemotactic factor (NCF) (PCT No. WO 89/10962).

Blockage of chemotaxis and neutrophil activation during inflammatory disease is a major therapeutic goal. Therapeutic intervention at various points of the inflammatory cascade is required to prevent injury to tissues. Induction of IL-1 and TNF production occurs within 30 minutes following exposure to, for example, LPS. Antibodies against the active, receptor-interacting site of TNF are effective intervenors in various animal models, for example, a pig model for septic shock. However, anti-TNF antibodies have to be administered very early in the course of disease to be effective.

What is needed, therefore, is a blocking antibody directed against a later-acting inflammatory protein. This would permit intervention at the secondary response level, subsequent to production of TNF, affording a larger window for diagnosis and preparation for treatment. In addition, a tandem therapeutic approach, employing anti-IL-8 antibodies in conjunction with anti-TNF antibodies, would increase the effectiveness wherein small amounts of TNF escaping anti-TNF binding would be secondarily neutralized.

BRIEF SUMMARY OF THE INVENTION

It has now been discovered that the active, receptor-interacting site of intact native human IL-8 resides within an 18 amino acid residue segment at the carboxy terminus of the mature 72 amino acid residue protein.

One aspect contemplated by this invention is a polypeptide analog of the IL-8 receptor-interacting site, having an amino acid residue sequence corresponding to the formula:

Cys-Leu-Asp-Pro-Lys-Glu-Asn-Trp-Val-Gln-Arg-Val-Val-Glu-Lys-Phe-Leu-Lys, designated p 50–67.

This invention also contemplates a polypeptide having an amino acid residue sequence corresponding to the formula:

(3–20), designated p 3–20.

Another aspect of this invention is an antibody that immunoreacts with (a) the IL-8 receptor-interacting site and (b) a polypeptide analog having an amino acid residue sequence corresponding to the formula for p 50–67.

A preferred embodiment of this invention is a monoclonal antibody that immunoreacts with the receptor-interacting site of IL-8 and the above-described polypeptide analog designated p 50–67.

A related aspect of this invention is an antibody that immunoreacts with (a) IL-8, and (b) a polypeptide having an amino acid residue sequence corresponding to the formula:

(3–20), designated p 3–20.

A preferred embodiment of this aspect is a monoclonal antibody that immunoreacts with IL-8 and the polypeptide p 3–20.

A method for detecting the presence of IL-8 in body fluids is another aspect contemplated by the present invention. This method comprises admixing an aliquot of body fluid with an antibody composition comprising an antibody molecule that immunoreacts with a carboxy terminal segment of IL-8 having an amino acid residue sequence corresponding to the formula:

Cys-Leu-Asp-Pro-Lys-Glu-Asn-Trp-Val-Gln-Arg-Val-Val-Glu-Lys-Phe-Leu-Lys.

Contact of the body fluid and the antibody composition is maintained for a time sufficient for an immunoreaction product to form. The IL-8-containing immunoreaction product formed is then detected.

A related aspect contemplates a method for detecting the presence of IL-8 in body fluids comprising admixing an aliquot of body fluid with an antibody composition comprising antibody molecules that immunoreact with an amino terminal segment of IL-8 having an amino acid residue sequence corresponding to the formula:

(3–20).

Contact of the body fluid and the antibody composition is maintained as before, and the IL-8-containing immunoreaction product formed is then detected.

Further contemplated by the present invention is a diagnostic system in kit form. The system comprises a package containing, in an amount sufficient to perform at least one assay, an antibody composition containing an antibody molecule population that immunoreacts with an antigenic determinant on an IL-8 molecule. This antibody composition can be in a liquid solution or attached to a solid-phase matrix. The system also contains a label for indicating the presence of the antibody molecules in the immunoreaction product formed.

In a preferred embodiment, the antibody composition contains a monoclonal antibody.

Also contemplated by this invention is a therapeutic composition that is suitable for preventing inflammation. Such a composition comprises an antibody that immunoreacts with (a) the receptor-interacting site of IL8, and (b) a polypeptide analog having an amino acid residue sequence corresponding to the formula:

Cys-Leu-Asp-Pro-Lys-Glu-Asn-Trp-Val-Gln-Arg-Val-Val-Glu-Lys-Phe-Leu-Lys, or biological equivalents thereof in a pharmaceutically acceptable excipient.

A related therapeutic composition contemplated by this invention comprises an antibody that immunoreacts with (a) IL-8, and (b) a polypeptide having an amino acid residue sequence corresponding to the formula:

(3–20), or biological equivalents thereof in a pharmaceutically acceptable excipient.

Further contemplated is a method for preventing inflammation in a patient. This method comprises administering to the individual a composition containing an antibody that immunoreacts with IL-8 and the above-described polypeptides designated p 50–67 or p 3–20, or biological equivalents thereof, in a pharmaceutically acceptable excipient.

Certain advantages attach to this invention, namely, a) intervention at a secondary level in the inflammatory cascade is now possible, permitting additional time for diagnosis and preparation for treatment, and b) more complete and effective intervention is possible by combining the previously known method utilizing anti-TNF antibodies and the method of this invention to secondarily neutralize TNF molecules that escape the anti-TNF antibody binding.

Still further embodiments and advantages of the invention will become apparent to those skilled in the art upon reading the entire disclosure contained herein.

BRIEF DESCRIPTION OF THE DRAWINGS

In the drawings, forming a portion of this disclosure.

DETAILED DESCRIPTION

A. Definition of Terms

Amino Acid: All amino acid residues identified herein are in the natural L-configuration. In keeping with standard polypeptide nomenclature, *J. Biol. Chem.*, 243:3557–59, (1969), abbreviations for amino acid residues are as shown in the following Table of Correspondence:

| TABLE OF CORRESPONDENCE | | |
|---|---|---|
| SYMBOL | | |
| 1-Letter | 3-Letter | AMINO ACID |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| e C | Cys | L-cysteine |

It should be noted that all amino acid residue sequences are represented herein by formulae whose left to right orientation is in the conventional direction of amino-terminus to carboxy-terminus. Furthermore, it should be noted that a dash at the beginning or end of an amino acid residue sequence indicates a bond to a radical such as H and OH (hydrogen and hydroxyl) at the amino- and carboxy-termini, respectively, or a further sequence of one or more amino acid residues up to a total of about fifty residues in the polypeptide chain.

Polypeptide and Peptide: Polypeptide and peptide are terms used interchangeably herein for a relatively low molecular weight, i.e., about 210 daltons to about 10 kD amino acid residue sequence and designate a linear series of no more than about 50 amino acid residues connected one to the other by peptide bonds between the alpha-amino and carboxy groups of adjacent residues.

Protein: Protein is a term used herein to designate a linear series of greater than 50 amino acid residues connected one to the other as in a polypeptide.

Pharmaceutically acceptable refers to molecular entities and compositions that do not produce an allergic or similar untoward reaction, such as gastric upset, dizziness and the like, when administered to a human.

B. Polypeptide Analog

Contemplated by this invention is an IL-8-related polypeptide that mimics certain functions of the active, receptor-interacting site of the native IL-8 molecule, having an amino acid residue sequence corresponding to the formula:

Cys-Leu-Asp-Pro-Lys-Glu-Asn-Trp-Val-Gln-Arg-Val-Val-Glu-Lys-Phe-Leu-Lys.

The polypeptide mimics the functions of IL-8 by promoting calcium mobilization in polymorphonuclear neutrophils, inducing elastase release, and when injected into rabbits, promoting chemotaxis of neutrophils at a concentration of $10^{-1}$M. The polypeptide, unlike IL-8, does not promote F-actin polymerization, which results under IL-8-receptor occupancy.

The polypeptide of this invention contains about 18 amino acid residues. Additional polypeptides, shorter in length than 18 amino acid residues are contemplated in order to more accurately define the precise active site. It is now known, for example, that a polypeptide analog containing amino acid residues 57 to 72 of the native IL-8 is inactive. Thus, a portion of the active site has to reside in or be conformationally directed by amino acid residues found in the first seven residues of the active site as presently defined.

A polypeptide sequence of this invention can differ from the natural sequence by the sequence being modified by terminal-$NH_2$ acylation, e.g., acetylation, or thioglycolic acid amidation, by terminal-carboxylamidation, e.g., with ammonia, methylamine, and the like.

1. Polypeptide Synthesis

A polypeptide of the present invention can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in J. M. Steward and J. D. Young, "Solid Phase Peptide Synthesis", W. H. Freeman Co., San Francisco, 1969; M. Bodanszky, et al., "Peptide Synthesis", John Wiley & Sons, Second Edition, 1976 and J. Meienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, these methods comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final polypeptide.

2. Activity Assays

Chemically synthesized polypeptide analogs must possess the active status of the native active, receptor-interacting region of IL-8. To insure that activity is present the following tests are performed.

1) $Ca^{++}$ mobilization in indo-1-AM-labeled neutrophils,
2) Elastase release in neutrophils, using a fluorescent method previously described [*J. Biol. Chem.*, 260:11461 (1985)],
3) Measuring neutrophil shape change by the decrease in right angle light scatter (done in parallel with $Ca^{++}$ determination),
4) Chemotactic capacity as measured by injection into rabbit skin and light microscopy of a biopsy 4 hours later.

3. Polypeptides

Also contemplated by this invention is a polypeptide having an amino acid residue sequence corresponding to the formula:

(3–20), designated p 3–20.

Polypeptide p 3–20 is useful to induce antibodies of this invention that immunoreact with IL-8 as described further herein.

C. Antibodies

The term "antibody" refers to a receptor molecule produced by B cells that immunoreacts with and binds to an antigen ligand to form an immunoreactant. It is a member of a family of glycosylated proteins called immunoglobulins, which can specifically combine with an antigen.

The term "antibody" in its various grammatical forms is also used herein to refer to immunologically active portions of immunoglobulin molecules, i.e., molecules that contain an antibody combining site or paratope.

Exemplary antibody molecules are intact immunoglobulin molecules, substantially intact immunoglobulin molecules and those portions of an immunoglobulin molecule that contain the paratope, including those portions known in the art as Fab, Fab', F(ab')$_2$ and F(v).

Fab and F(ab')$_2$ portions of antibodies are prepared by the proteolytic reaction of papain and pepsin, respectively, on substantially intact antibodies by methods that are well known. See for example, U.S. Pat. No. 4,342,566 to Theofilopolous and Dixon. Fab' antibody portions are also well known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules are preferred, and are utilized as illustrated herein.

The phrase "monoclonal antibody" (MoAb) designates an antibody produced by clones of a single cell called a hybridoma that secretes but one kind of antibody molecule. The hybridoma cell is formed by fusing an antibody-producing cell and a myeloma or other self-perpetuating cell line. Such antibodies were first described by Kohler and Milstein, *Nature,* 256:495–497 (1975), which description is incorporated by reference.

"Polyclonal" antibodies (Pab) are antibodies produced by clones derived from different cells that secrete different antibodies that bind to a plurality of epitopes of the immunogenic molecule.

1. Polypeptide Immunogen

The term "immunogen", as used herein, describes an entity that induces antibody production in the host animal. In some instances, the antigen and immunogen are the same entity, while in other instances, the two entities are different.

The word "inoculum" in its various grammatical forms is used herein to describe a composition containing a polypeptide of this invention, preferably Pep-1 or Pep-3 as shown in Table 1, as an active ingredient used for the preparation of antibodies against IL-8. When a polypeptide is used to induce antibodies it is to be understood that the polypeptide may be used alone, linked to a carrier or as a multimer, but for ease of expression, these alternatives will not always be expressed hereinafter.

For a polypeptide that contains fewer than about 35 amino acid residues, it is preferable to use the peptide bound to a carrier for the purpose of inducing the production of antibodies.

When coupled to a carrier to form what is known in the art as a carrier-hapten conjugate, a polypeptide of the present invention is capable of inducing antibodies that immunoreact with and neutralize IL-8. Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as poly amino acids such as poly (D-lysine: D-glutamic acid), and the like.

As is also well known in the art, it is often beneficial to bind a synthetic polypeptide to its carrier by means of an intermediate, linking group. As noted above, glutaraldehyde is one such linking group. However, when cysteine is used, the intermediate linking group is preferably an m-maleimidobenxoyl N-hydroxy succinimide (MBS).

Additionally, MBS may be first added to the carrier by an ester-amide interchange reaction as disclosed by Liu et al., supra. Thereafter, the addition can be followed by addition of a blocked mercapto group such as thiolacetic acid ($CH_3COSH$) across the maleimido-double bond. After cleavage of the acyl blocking group, a disulfide bond is formed between the unblocked linking group mercaptan and the mercaptan of the added cysteine residue of the synthetic polypeptide.

Other means of immunopotentiation include the use of liposomes and immuno-stimulating complex (ISCOM) particles. The unique versatility of liposomes lies in their size adjustability, surface characteristics, lipid composition and ways in which they can accommodate antigens. In ISCOM particles, the cage-like matrix is composed of Quil A, extracted from the bark of a South American tree. A strong immune response is evoked by antigenic proteins or peptides attached by hydrophobic interaction with the matrix surface.

The choice of carrier is more dependent upon the ultimate use of the immunogen than upon the determinant portion of the immunogen, and is based upon criteria not particularly involved in the present invention. For example, if an inoculum is to be used in animals, a carrier that does not generate an untoward reaction in the particular animal should be selected.

In a preferred embodiment of this invention, the inoculum comprises the before-described polypeptide coupled to KLH via MBS.

2. Polyclonal Antibodies

To induce IL-8-neutralizing antibodies, an immunogenic amount of an inoculum of this invention, preferably containing peptide Pep-1 or Pep-3 as the active immunogen, is administered, typically by subcutaneous or intramuscular injection, to a mammal such as a mouse, rabbit, goat, horse, human and the like. In a preferred embodiment of this invention, administration was accomplished by multi-site subcutaneous injections into rabbits at days 1, 14 and 21.

The administered (inoculated) mammal is then maintained for a time period sufficient for the polypeptide present as active ingredient in the inoculum to induce elicitation of neutralizing anti-IL-8 antibodies. If desired, the antibodies elicited can then be harvested, using well-known techniques, and used in preparations for passive immunization (therapeutic administration of neutralizing antibodies) against IL-8 active site, or in diagnostic assays and systems to detect IL-8 in body samples.

The anti-peptide antibody so produced is oligoclonal with respect to IL-8, and thus has restricted epitope specificity relative to anti-IL-8 polyclonal antisera.

Preferably, a polyclonal antibody of this invention is in an immunopurified form. Immunopurified polyclonal antibody compositions are produced by immunoreacting (adsorbing) a polyclonal antisera onto a solid phase containing the polypeptide immunogen used to induce the polyclonal antisera, rinsing the non- or weakly-immunoreacting antibodies away from the solid phase, and subsequently eluting and collecting the specifically immunoreacted antibodies to form immunopurified antibody. Immunopurification is a generally well known method in the arts, and can be performed under a variety of conditions designed to produce a polyclonal antibody composition having a higher net affinity for the immunopurifying solid phase immunogen than the affinity of the starting polyclonal antisera. Exemplary immunopurification is described in Example 3D.

3. Monoclonal Antibodies

Suitable antibodies in monoclonal form, typically whole antibodies, can be prepared using hybridoma technology described by Niman et al., *Proc. Natl. Acad. Sci., U.S.A.,* 80:4949–4953 (1983), which description is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a polypeptide of this invention.

It is preferred that the myeloma cell line be from the same species as the lymphocytes. Typically, a mouse of the strain 129 GlX[+] is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 1500. Fused hybrids are selected by their sensitivity to HAT. Hybridomas secreting the antibody molecules of this invention are identified using the solid-phase radioimmunoassay (RIA) described in Example 4.

A monoclonal antibody composition of the present invention can be produced by initiating a monoclonal hybridoma culture comprising a nutrient medium containing a hybridoma that secretes antibody molecules of the appropriate polypeptide specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/1 glucose, 20 mM glutamine, and 20% fetal calf serum. An exemplary inbred mouse strain is the Balb/c.

The monoclonal antibody compositions produced by the above method can be used, for example, in diagnostic and therapeutic modalities wherein formation of an IL-8-containing immunoreaction product is desired.

D. Diagnostic Methods

The present invention contemplates any method that results in detecting, in a body fluid such as blood plasma or serum, a receptor-interactive site of IL-8, and thus, IL-8, using an antibody composition of this invention.

The method for detecting IL-8 by this means comprises the formation of an immunoreaction product between a carboxy terminal segment of IL-8 in the harvested vascular fluid and an anti-IL-8 active site antibody molecule, as disclosed herein, and the subsequent detection of the immunoreaction product so formed.

Alternatively, the method for detecting IL-8 comprises the formation of an immunoreaction product between an amino terminal segment of IL-8, namely the p 3–20 defined region, in the harvested vascular fluid and an anti-IL-8 antibody molecule as disclosed herein, and the subsequent detection of the immunoreaction product so formed.

Those skilled in the art will understand that there are numerous well known clinical diagnostic chemistry procedures that can be utilized to form detectable immunocomplexes. Thus, while exemplary assay methods are described herein, the invention is not so limited.

One method contemplated for detecting the presence of IL-8 in a body fluid, comprises the steps of:

(a) admixing an aliquot of body fluid with an antibody composition that immunoreacts with a carboxy terminal segment of IL-8 having an amino acid residue sequence corresponding to the formula:
Cys-Leu-Asp-Pro-Lys-Glu-Asn-Trp-Val-Gln-Arg-Val-Val-Glu-Lys-Phe-Leu-Lys.

(b) maintaining the immunoreaction admixture under biological assay conditions for a time period sufficient to form an immunoreaction product; and (c) detecting the presence of said immunoreaction product, and thereby the presence of IL-8.

In a related IL-8 detection method, the above steps are conducted except that the antibody composition admixed in step (a) contains antibody molecules that immunoreact with an amino terminal segment of IL-8 having an amino acid residue sequence corresponding to the formula:
(3–20).

To perform diagnostic assays, as described, diagnostic systems in kit form are contemplated.

E. Diagnostic Systems

A diagnostic system of the present invention useful for in vitro detection of the presence of IL-8 in vivo is contemplated. The system comprises a composition containing antibody molecules that immunoreact with an active, receptor-interacting site of IL-8. The antibody molecules are linked to an in vitro indicating means, such as an enzyme indicating means.

The diagnostic system comprises a package containing antibody molecules that immunoreact with an epitope present in a carboxy terminal segment of IL-8. Most preferred are antibodies capable of immunoreacting with an epitope present in a sequence of not more than 18 amino acid residues in length and including the amino acid residue sequence of the native IL-8 molecule from residue 50 to residue 67.

A diagnostic system of the present invention in kit form includes, in an amount sufficient to perform at least one assay, a composition containing polyclonal or monoclonal anti-IL-8 active, receptor-interacting site antibody molecules or fragments thereof, as a separately packaged reagent, together with a label that indicates the presence of an immunoreaction product. Instructions for use of the packaged reagent are also typically included.

A related diagnostic system useful for in vitro detection of the presence of IL-8 comprises a composition containing antibody molecules that immunoreact with an epitope present on the amino terminal segment of IL-8 defined by the polypeptide p 3–20.

This related diagnostic system in kit form includes, in an amount sufficient to perform at least one assay, a composition containing polyclonal or monoclonal anti-IL-8 antibody molecules or fragments thereof immunospecific for the polypeptide p 3–20, together with a label that indicates the presence of an immunoreaction product. Instructions for use of the packaged reagent of this embodiment are also typically included.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like. Also included, in one form or another, may be charts, graphs and the like of predetermined concentration levels correlating specific physiological conditions to levels of IL-8.

A diagnostic system of the present invention also includes a label or indicating means capable of signaling the formation of a specifically bound complex containing an antibody molecule of the present invention.

Further preferred are kits wherein the antibody molecules are linked to an enzyme indicating means, such as horseradish peroxidase (HRPO).

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel methods and/or systems.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.,* 73:3–46 (1981). The techniques of protein conjugation or coupling through activated functional groups are particularly applicable. See, for example, Avrameas, et al., *Scand. J. Immunol.,* Vol. 8, Suppl. 7:7–23 (1978), Rodwell et al., *Biotech.,* 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention but is not itself an antibody molecule of the present invention. Exemplary specific binding agents are antibody molecules, complement proteins or fragments thereof, protein A and the like. Preferably, the specific binding agent can bind the antibody molecule of this invention when it is present as part of a complex.

In preferred embodiments the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect, for example, the presence or quantity of IL-8 by assaying for immunoreactive molecules in a body fluid sample such as serum or plasma. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. No. 3,654,090; U.S. Pat. No. 3,850,752; and U.S. Pat. No. 4,016,043, which are all incorporated herein by reference.

Thus, in preferred embodiments, the antibody or antigen reagent component can be affixed to a solid matrix to form a solid support that is separately packaged in the subject diagnostic systems. The reagent is typically affixed to the solid matrix by adsorption from an aqueous medium, although other modes of affixation, well known to those skilled in the art, can be used.

Useful solid matrices are well known in the art. Such materials include the cross-linked dextran available under the trademark SEPHADEX from Pharmacia Fine Chemicals (Piscataway, N.J.); agarose; polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packages discussed herein in relation to diagnostic systems are those customarily utilized in diagnostic systems. Such packages include glass and plastic (e.g., polyethylene, polypropylene and polycarbonate) bottles, vials, plastic and plastic-foil laminated envelopes and the like.

F. Therapeutic Compositions

Also contemplated by this invention is a therapeutic composition suitable for inhibiting IL-8 binding and thereby preventing inflammation, comprising an antibody that immunoreacts with (a) the receptor-interacting site of IL-8, and (b) a polypeptide analog having an amino acid residue sequence corresponding to the formula:

Cys-Leu-Asp-Pro-Lys-Glu-Asn-Trp-Val-Gln-Arg-Val-Val-Glu-Lys-Phe-Leu-Lys, or biological equivalents thereof in a pharmaceutically acceptable excipient. This composition attains its therapeutic effect by combining with and neutralizing the active site of IL-8.

A related therapeutic composition is contemplated that is suitable for inhibiting IL-8 binding and thereby preventing IL-8-mediated events such as inflammation, comprising an antibody that immunoreacts with (a) IL-8, and (b) a polypeptide having an amino acid residue sequence corresponding to the formula:

(3–20), or biological equivalents thereof in a pharmaceutically acceptable excipient. This composition attains its therapeutic effect by immunoreacting with IL-8 and thereby interfering with (neutralizing) the active site of IL-8. Insofar as p 3–20 is located at the amino terminus of IL-8 as compared to the polypeptide analog p 50–67 and was not effective as an IL-8 active-site analog, it is believed that p 3–20 does not represent an active site analog. Thus antipeptide antibodies immunospecific for p 3–20 do not immunoreact with the active site, per se, but bind (immunoreact) with IL-8 in a manner that interferes with and thereby neutralizes the binding activity of IL-8.

Thus, in another embodiment, a therapeutic composition is contemplated that is suitable as an analog to IL-8 having the capacity to function as defined herein for a polypeptide analog, comprising a polypeptide analog having an amino acid residue sequence corresponding to the formula:

(50–67), or biological equivalents thereof in a pharmaceutically acceptable excipient. This composition attains its therapeutic effect by mimicking the active site of IL-8 and thereby exhibiting the biological activity of IL-8 as defined herein for a polypeptide analog.

The preparation of therapeutic compositions which contain antibody molecules or polypeptides as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

An antibody or polypeptide can be formulated into the therapeutic composition as neutralized pharmaceutically acceptable salt forms. Pharmaceutically acceptable salts include the acid addition salts (formed with the free amino groups of the antibody molecule) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

G. Methods for Inhibiting the Inflammatory Response

Also contemplated by this invention, is a method for inhibiting IL-8 activity and thereby preventing inflammation in a patient, comprising administering to the patient a composition containing an antibody that immunoreacts with (a) the receptor-interacting site of IL-8, and (b) a polypeptide analog having an amino acid residue sequence corresponding to the formula:

Cys-Leu-Asp-Pro-Lys-Glu-Asn-Trp-Val-Gln-Arg-Val-Val-Glu-Lys-Phe-Leu-Lys, or biological equivalents thereof in a pharmaceutically acceptable excipient.

In a related embodiment, the invention contemplates a method for inhibiting IL-8 activity and thereby preventing inflammation in a patient, comprising administering to the patient a composition containing an antibody that immunoreacts with (a) IL-8, and (b) a polypeptide having an amino acid residue sequence corresponding to the formula: (3–20), or biological equivalents thereof in a pharmaceutically acceptable excipient.

The therapeutic antibody molecule-containing compositions are conventionally administered intravenously, as by injection of a unit dose, for example. The term "unit dose" when used in reference to a therapeutic composition of the present invention refers to physically discrete units suitable as unitary dosages, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient without adverse side affects, and degree of inhibition of interaction desired between IL-8 and the appropriate cell type. Precise amounts of active antibody required to be administered depend on the judgment of the practitioner and are peculiar to each individual. However, suitable dosage ranges are of the order of 0.1 to 40 milligrams, preferably 10 to 20 milligrams, and most preferably about 15 milligrams, of antibody per kilogram bodyweight of individual and depend on the route of administration.

It is expected that a single dose of about 15 mg/kg body weight of an individual will be effective. Suitable regimes for booster shots, if required, are also variable, but are typified by an initial administration followed by repeated doses at predetermined intervals by a subsequent injection or other administration. Alternatively, continuous intravenous infusion sufficient to maintain concentrations of 15 milligrams per kilogram body weight in the blood are contemplated.

The following examples are intended to illustrate, but not limit, the present invention.

EXAMPLES

The following examples are intended to illustrate, but not limit, the present invention.

1. Polypeptide Synthesis

Polypeptides corresponding to the amino acid residue sequence 3–20, 50–67 and 57–72, designated hereafter as Pep-3, Pep-1 and Pep-2, respectively, of IL-8 were synthesized by the classical solid-phase technique described by Merrifield, *Adv. Enzymol.*, 32:221–296 (1969) as adapted for use with a Model 430A automated peptide synthesizer (Applied Biosystems, Foster City, Calif.). Polypeptide resins were cleaved by hydrogen fluoride, extracted and analyzed for purity by high-performance liquid chromatography on a reverse-phase C18 column manufactured by Water Associates, Milford, Mass.

The amino acid residue sequence of the polypeptides named above is shown in Table 1.

TABLE 1

| Formula Designation[1] | Sequence Origin with IL-8 | Amino Acid Residue Sequence |
| --- | --- | --- |
| Pep-1 | 50-67 | CLDPKENWVQRVVEKFLK |
| Pep-2 | 57-72 | WVQRVVEKFLKRAENS |
| Pep-3 | 3-20 | KELRCQCIKTYSKPFHPK |

[1]Polypeptides Pep-1, Pep-2 and Pep-3 are also referred to herein as p 50-67, p 57-72 and p 3-20, respectively.

2. Neutrophil Activation by an IL-8 Related Synthetic Polypeptide

A. In Vitro Assays (1) Preparation of Cells

Blood was collected after informed consent from medication-free normal volunteers and anticoagulated with a mixture of 0.14M citric acid, 0.2M trisodium citrate, and 0.22M dextrose. The anticoagulated blood was centrifuged at 800×g for 15 minutes at room temperature and the platelet-rich plasma supernatant was discarded. The pelleted erythrocytes, mononuclear and polynuclear cells were resuspended and diluted with a volume equal to the starting blood volume with chilled 0.14M PBS, pH 7.4. The peripheral blood mononuclear cells (PBMC) were depleted from the diluted cell suspension by centrifugation on low endotoxin Ficoll-Hypaque (Sigma Chem. Corp., St. Louis, Mo.) at 400×g for 10 minutes at 18 degrees C. (18° C.).

The polynuclear cells (neutrophils) in the PBMC-depleted cell suspension were then recovered by dextran sedimentation. The resulting cell pellet containing neutrophils was resuspended at a concentration of $1.5 \times 10^7$ cells/milliliter (ml) in calcium-free Hanks Balanced Salt Solution (HBSS) (Sigma Chem. Corp.). The resuspended cell suspension was maintained on ice and used within two hours of isolation.

(2) Calcium Mobilization

The resultant cell suspension containing isolated IL-8 receptor-expressing neutrophils was fluorescently labeled with Indo-1-AM (Molecular Probes, Eugene, Oreg.). A five micromolar (uM) solution of Indo-1-AM dissolved in 0.1% final concentration of dimethyl sulfoxide (DMSO) was admixed with $1 \times 10^7$ neutrophils/ml in calcium-free HBSS, prepared in (1) above, and the admixture was maintained for 30 minutes at 37° C. to form fluorescently labeled neutrophils. After the maintenance period, the Indo-1-AM labeled cell suspension was washed two times with calcium-free HBSS. The resultant fluorescently labeled and washed neutrophils were resuspended to a final concentration of $2 \times 10^6$ cells/ml in HBSS containing 10 mM Hepes, 1.5 mM calcium and 1 gram of glucose. The cell suspension was then pre-warmed by maintenance at 37° C. for 2 minutes.

Aliquots of the fluorescently labeled pre-warmed neutrophil cell suspension were separately admixed with $1 \times 10^{-12}$M of the synthetic polypeptide, Pep-1, produced in Example 1, (TABLE 1), human recombinant IL-8 derived from either endothelial cells (Biosource, Westlake Village, Calif.) or from monocytes (Sandoz, Basel, Switzerland), or $1 \times 10^{-8}$M of the synthetic polypeptide, Pep-2, produced in Example 1. Each admixture was subjected to cell fluorometry through which the effects of synthetic peptides or IL-8 on calcium mobilization in neutrophils were evaluated. Calcium mobilization was measured in each admixture by detecting changes in fluorescence over time on a SLM 8000 fluorometer. The fluorometer was equipped with a 340 nanometer (nm) wavelength excitation filter, a 400 nm wavelength emission filter in channel A which represents calcium-bound Indo-1-AM, and a 485 nm wavelength emission filter in channel B which represents free Indo-1-AM. The ratio of detected fluorescence in channel A to channel B (denoted as F ratio) equals the value of the amount of intracellular calcium.

Figure 1:
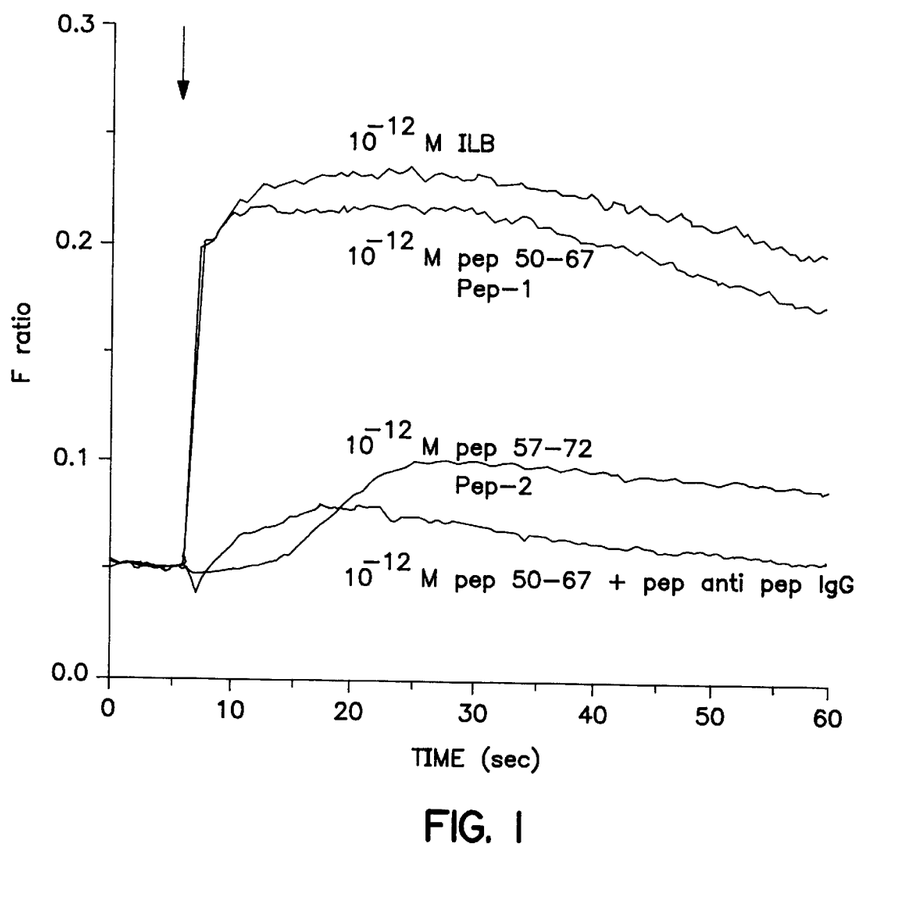
FIG. 1 illustrates the effects of IL-8 or of synthetic polypeptides corresponding to the amino acid residue sequence 50–67 and 57–72 of IL-8 on neutrophil activation as measured by calcium mobilization. The F ratio, which equals the value of intracellular calcium, is plotted on the Y-axis against time in seconds of post-IL-8 or peptide treatment plotted on the X-axis. IL-8 and the synthetic polypeptide 50–67, also called Pep-1, induce calcium mobilization in neutrophils whereas the synthetic polypeptide 57–72, also called Pep-2, does not. The calcium mobilization induced by Pep-1 treatment of neutrophils is inhibited by anti-Pep-1 polyclonal antibodies.

The results of this assay, shown in FIG. 1, indicate that calcium mobilization in Indo-1-AM labeled neutrophils was increased ten seconds after treatment with the synthetic polypeptide, Pep-1, as measured by fluorometry and calculation of the F ratios as described above. The results are compared to F ratios calculated from neutrophils treated with either human recombinant IL-8 or the synthetic peptide, Pep-2. Both Pep-1 and human recombinant IL-8 induce calcium mobilization which saturates 20 seconds after treatment. In contrast, the synthetic peptide, Pep-2, does not promote calcium mobilization. The effect of Pep-1 on calcium mobilization in neutrophils mimics intact human recombinant IL-8 whereas the Pep-2 fails to promote the same response.

The results of this study indicate that the first seven amino-terminal amino acid residues of Pep-1 are responsible for the ability of Pep-1 to bind to the IL-8 receptor. Thus, additional polypeptides of this invention have an amino acid residue sequence length in the range of 7 to 30, and preferably no more than 20 to 25 residues, and contain the sequence CLDPKEN. Preferably, these peptides have an overall sequence that corresponds, and preferably identical to, IL-8. It is also preferred that these peptides bind to the IL-8 receptor, as evidenced by their ability to competitively inhibit IL-8 binding to the receptor, but not induce neutrophil activation as described in the above Section B2 Activity Assays. Exemplary peptides are shown in Table 2 below.

Table 2

CLDPKEN
CLDPKENW
CLDPKENWV
CLDPKENWVQ
CLDPKENWVQR
CLDPKENWVQRV
CLDPKENWVQRVV
CLDPKENWVQRVVE
CLDPKENWVQRVVEK
CLDPKENWVQRVVEKF
CLDPKENWVQRVVEKFL (3) Right Angle Light Scatter Aliquots of isolated neutrophils, prepared in (1) above, were treated with either $1\times10^{-12}$M IL-8 related synthetic polypeptides as performed in (2) above. The treated neutrophils, subjected to fluorometry in (2) above, were also analyzed concurrently for morphological changes in response to cellular activation. The measurement of right angle light scatter at an excitation and emission spectrum of 340 nm is an indirect means of determining shape changes. Treatment of neutrophils with Pep-1 resulted in a decrease in right angle light scatter comparable to that seen with intact IL-8. Pep-1, thus, effected a shape change in parallel with increased calcium mobilization in neutrophils mimicking activation by IL-8.

(4) Elastase Release

Elastase release was determined with the fluorescent substrate oMe-succinimide-Ala-Ala-Pro-Val-methyl-coumaryl amide (Peninsula Laboratories). Aliquots of $2\times10^6$ isolated neutrophils/ml, as prepared in (1) above, were maintained at 37° C. for 2 minutes in the presence of $2\times10^{-5}$M of the fluorescent substrate dissolved in 0.1% DMSO and 1 microgram (ug)/ml cytochalasin B. Substrate treated aliquots of neutrophils were then separately admixed with synthetic polypeptides prepared in Example 1.

The resultant admixture was then subjected to fluorometric analysis as performed in (2) above on a SLM 8000 fluorometer equipped with a 380 nm wavelength excitation filter and a 4900 Angstrom emission filter. The elastase released from the peptide treated neutrophils was measured kinetically over a period of 2 minutes in a stirred cuvette maintained at 37° C. The total elastase content of the neutrophils was determined by cell lysis by 1% Triton X-100. Spontaneous elastase release was subtracted from the total to obtain a net elastase release.

The results of the elastase release assay indicate that Pep-1, at a concentration of 1×10–9M, promoted elastase release in neutrophils comparable to that seen with intact human recombinant IL-8. These results provide further support of Pep-1 containing the active site of IL-8, thereby mimicking IL-8 activation of neutrophils.

B. In Vivo Assays

Pep-1, prepared in Example 1, was dissolved in lipopolysaccharide-free phosphate buffered saline (PBS) and the solutions, in concentrations ranging from $1\times10^{-9}$M to $1\times10^{-11}$M, were injected into the skin of a rabbit. Human recombinant IL-8, prepared similarly, was injected into a separate skin area on the same rabbit. Injections of PBS alone served as a negative control. A second rabbit received similar injections of the solutions.

Skin corresponding to the areas of Pep-1, IL-8 and PBS injections were excised from the rabbits four hours post-injection. The excised skin samples were evaluated by light microscopy for the chemotaxis of neutrophils into the area of injection. Injections of Pep-1 resulted in a dose-dependent neutrophil chemotaxis that were not distinguishable from the influx induced by the same concentrations of IL-8. Neutrophils were not prevalent in areas receiving PBS injections.

3. Preparation of Polyclonal Antisera to an IL-8 Related Synthetic Polypeptide

A. Preparation of the Immunogen

The synthetic polypeptide, Pep-1, prepared in Example 1 was coupled to keyhole limpet hemocyanin (KLH) through the N-terminal cysteine residue on Pep-1 to form Pep-1-KLH conjugates. KLH was dialyzed against a solution of 10 mM PBS and the resultant dialyzed KLH was adjusted to a concentration of 20 milligrams (mg)/ml. Three mg of m-Maleimidobenzoyl N-Hydroxysuccinimide Ester (MBS) (Pierce Biochemicals, Rockford, Ill.) was dissolved in 5 ml of dimethyl formamide (Pierce Biochemicals). Eight-five microliters (ul) of the resultant MBS solution were admixed with 200 ul of the KLH solution to form a KLH-MBS admixture which was maintained at 25° C. for 30 minutes.

The KLH-MBS admixture was thereafter chromatographed through a G-25 Sephadex column (Pharmacia, Piscataway, N.J.) and 1 ml fractions of MBS-treated KLH were collected. One ml of the chromatographed KLH was then admixed with 1 ml of a 5 mg/ml solution of Pep-1 previously dissolved in PBS to form a Pep-1-KLH conjugate immunogen. The pH of the Pep-1-KLH admixture was adjusted to pH 7.0 and then maintained at 25° C. for three hours.

A Pep-3-KLH conjugate immunogen was similarly prepared as above except using the synthetic polypeptide Pep-3 in place of Pep-1.

B. Immunization and Collection of Polyclonal Antisera

The Pep-1-KLH immunogen prepared in Example 3A was emulsified in Complete Freund's Adjuvant (CFA) and the Pep-1-KLH antigens were incorporated into the emulsion at a concentration of 200 ug/1.5 ml. Two rabbits were each injected with 1.5 ml of the prepared emulsion after pre-immune serum samples were collected. The total volume of the emulsion dose was equally divided for subcutaneous administration to the back, shoulders, and rump of a rabbit.

The rabbits received a booster injection of the Pep-1-KLH immunogen emulsified in Incomplete Freund's adjuvant (IFA) on day 14. On day 21, each rabbit received an intraperitoneal injection of 1 ml of a 10 mg/ml solution of free Pep-1 dissolved in 1.2 ml PBS containing 0.8 ml aluminum hydroxide. Serum samples were collected from each immunized rabbit 7 and 14 days following the third injection and were analyzed by Western blot described in C. below for the detection of Pep-1 specific antibodies.

Serum samples were produced in a similar manner using rabbits immunized with the Pep-3-KLH immunogen of Example 3A to form Pep-3 specific antibodies that were characterized as described in C. below.

C. Screening of Polyclonal Antisera by Western Blot Analysis

Samples of human recombinant IL-8, Pep-1 and Pep-3 at a concentration of 100 ng/ml were separated by gel electrophoresis and were transferred onto nitrocellulose for subsequent immunoblotting analysis. The nitrocellulose filter was admixed with antibody blocking buffer (20 mM sodium phosphate, pH 7.5, 0.5M sodium chloride, 1% bovine serum albumin, and 0.05% Tween 40) for 3 to 12 hours at room temperature. Sera collected from rabbits, prepared in Example 3B, believed to contain antibody immunoreactive with Pep-1 or with Pep-3 was diluted 1:500 in the antibody blocking buffer and admixed with the nitrocellulose. The resultant admixture was maintained for 12 hours at room temperature to allow the formation of an immunoreaction product on the solid phase.

Pre-immune sera from the same rabbits was tested simultaneously on separate samples to serve as a negative control. The nitrocellulose was then washed three times in excess volumes of antibody blocking buffer. The washes were followed by admixture of the nitrocellulose with anti-rabbit IgG conjugated to horseradish peroxidase (HRP) (Sigma Chem. Corp.) at a 1:500 dilution in antibody blocking buffer for one hour at room temperature to allow the HRP-labeled IgG to bind to any immunoreaction product present in the solid phase on the nitrocellulose. The nitrocellulose was then washed as described herein and developed by treatment with 4-chloro-1-naphthol as a substrate in order to visualize the label and therefore any immunoreaction product on the nitrocellulose.

Polyclonal antisera containing antibodies immunoreactive with IL-8, Pep-1 and Pep-3 were then evaluated in their ability to inhibit IL-8 function as described in Example 5.

D. Immunoaffinity Purification of Polyclonal Antibodies

Anti-Pep-1 and anti-Pep-3 antibodies prepared as polyclonal antisera as described in Example 3C were immunoaffinity purified using immobilized polypeptide in the solid phase as follows.

Polypeptides Pep-1 and Pep-3 were each separately coupled to cyanogen-bromide (CNBr)-activated Sepharose 4B (Pharmacia) at a concentration of 3 mg protein to 1 ml gel in coupling buffer (0.5M NaCl and 0.05M borate at pH 8.5) overnight at 4° C. to form a polypeptide-Sepharose suspension. The suspension was packed into a column and washed with coupling buffer to remove unbound polypeptide according to manufacturer's instructions. Polyclonal antisera was admixed with a buffer solution containing 0.1M NaCl, 2 mM ethylene diamine tetraacetic acid (EDTA), 2 mM benzamidine, 0.02% $NaN_3$, 0.02% Tween-20, 0.02M Tris-HCl at pH 7.4. The buffered sera was then passed over the prepared polypeptide-Sepharose column to immobilize anti-polypeptide antibodies on the antibody column and separate polypeptide specific antibodies from non-specific or weakly specific antibodies, and other serum components. The polypeptide column containing immobilized antibody was subsequently washed to further remove unbound antibodies and other protein. Immobilized antibody was then eluted from the column with 3M sodium thiocyanate (NaSCN) in 1.0M NaCl, 4 mM benzamidine, 2 mM EDTA, 0.02% $NaN_3$, and 0.05M Tris-HCl at pH 7.0. The eluted and purified antibody was determined to be greater than 95% pure when analyzed using sodium dodecyl sulfate-polyacrylamide gel electrophoresis (SDS-PAGE).

4. Preparation of Monoclonal Antibodies to an IL-8 Related Synthetic Polypeptide A. Generation of Anti-Pep-1 Hybridomas The synthetic polypeptide, Pep-1, is prepared as an immunogen according to Example 3. Balb/c ByJ mice (Scripps Clinic and Research Foundation Vivarium, La Jolla, Calif.) are immunized intraperitoneally (i.p.) with 50 ug of prepared Pep-1-KLH immunogen in CFA followed by a second and third immunization using the same Pep-1-KLH immunogen, each about three weeks apart, in IFA. The mice receive a boost of 50 ug of prepared Pep-1-KLH immunogen intravenously (i.v.) in normal saline 4 days prior to fusion and a second similar perfusion boost one day later.

The animals so treated are sacrificed and the spleen of each mouse is harvested. A spleen cell suspension is then prepared. Spleen cells are then extracted from the spleen cell suspension by centrifugation for about 10 minutes at 1000 r.p.m., at 23° C. Following removal of supernatant, the cell pellet is resuspended in 5 ml cold $NH_4Cl$ lysing buffer, and was incubated for about 10 minutes.

To the lysed cell suspension are admixed 10 ml Dulbecco's Modified Eagle Medium (DMEM) (GIBCO) and HEPES [4-(2-hydroxyethyl)-1-piperidineethanesulfonic acid] buffer, and that admixture is centrifuged for about 10 minutes at 1000 r.p.m. at 23° C.

The supernatant is decanted, the pellet is resuspended in 15 ml of DMEM and HEPES, and is centrifuged for about 10 minutes at 1000 r.p.m. at 23° C. The above procedure is repeated.

The pellet is then resuspended in 5 ml DMEM and HEPES. An aliquot of the spleen cell suspension is then removed for counting. Fusions are accomplished in the following manner using the non-secreting mouse myeloma cell line P3X63Ag8.653.1, a subclone of line P3x63Ag 8.653 (ATCC 1580). Using a myeloma to spleen cell ratio of about 1 to 10 or about 1 to 5, a sufficient quantity of myeloma cells are centrifuged into a pellet, washed twice in 15 ml DMEM and HEPES, and centrifuged for 10 minutes at 1000 r.p.m. at 23° C.

Spleen cells and myeloma cells are combined in round bottom 15 ml tubes. The cell mixture is centrifuged for 10 minutes at 1000 r.p.m. at 23° C., and the supernatant is removed by aspiration. Thereafter, 200 ul of 50 percent (weight per volume) aqueous polyethylene glycol 4000 molecular weight (PEG; ATCC Baltimore, Md.) at about 37° C. are admixed using a 1 ml pipette with vigorous stirring to disrupt the pellet, and the cells are gently mixed for between 15 and 30 seconds. The cell mixture is centrifuged 4 minutes at 700 r.p.m.

At about 8 minutes for the time of adding the PEG, 5 ml of DMEM plus HEPES buffer are admixed slowly to the pellet, without disturbing the cells. After 1 minute, the resulting admixture is broken up with a 1 ml pipette, and is incubated for an additional 4 minutes. This mixture is centrifuged for 7 minutes at 1000 r.p.m. The supernatant is decanted, 5 ml of HT (hypoxanthine/thymidine) medium are slowly admixed to the pellet, and the admixture is maintained undisturbed for 5 minutes. The pellet is then broken into large chunks, and the final cell suspension is placed into T75 flasks (2.5 ml per flask) into which 7.5 ml HT medium have been placed previously. The resulting cell suspension is incubated at 37° C. to grow the fused cells. After 245 hours 10 ml of HT medium are admixed to the flasks, followed 6 hours later by admixture of 0.3 ml of 0.04 mM aminopterin. 48 hours after fusion, 10 ml of HAT (hypoxanthine/ aminopterin/thymidine) medium are admixed to the flasks.

Three days after fusion, viable cells are plated out in 96-well tissue culture plates at about $2 \times 10^4$ viable cells per well (768 total wells) in HAT buffer medium as described in Kennett et al., *Curr. Top. Microbiol. Immunol.*, 81:77 (1978). The cells are fed seven days after fusion with HAT medium and at approximately 4–5 day intervals thereafter as needed with HT medium. Growth is followed microscopically, and culture supernatants are collected about two weeks later and assayed for the presence of Pep-1-specific antibody by solid phase radioimmunoassay (RIA).

Briefly, 50 μl of PBS containing 5 μg/ml of the prepared Pep-1-KLH immunogen is admixed into the wells of microtiter plates. The plates are maintained overnight (about 16 hours) at 4° C. to permit the Pep-1-KLH immunogen to adhere to well walls. After washing the wells four times with SPRIA buffer (2.68 mM KCl, 1.47 mM $KH_2PO_4$, 137 mM NaCl, 8.03 mM $Na_2HPO_4$, 0.05% Tween-20, 0.1 KIU/ml Traysol, 0.1% BSA, 0.015% $NaN_3$), 200 μl of SPRIA buffer containing 3% normal goat serum (NGS) and 3% bovine serum albumin (BSA) are admixed to each well to block excess protein binding sites. The plates are maintained for 30 minutes at 20° C., the wells emptied by shaking, and blotted dry to form a solid-support, i.e., a solid matrix to which Pep-1-KLH immunogen is operatively affixed.

To each well is then admixed 50 ul of hybridoma tissue culture supernatant to form a solid-liquid phase immunoreaction admixture. The admixture is maintained for 2 hours at 37° C. to permit formation of solid-phase immunoreaction products. After washing the wells as described hereinbefore, 50 ul of $^{125}$I-labelled goat anti-mouse IgG at (Cappel Laboratories, Downington, Pa.) 0.25 ug protein per ml are admixed to each well to form a labelling reaction admixture. That admixture is maintained for 1 hour at 37° C. to permit formation of $^{125}$I-labelled solid-phase immunoreaction products. After washing the wells as previously described, the amount of $^{125}$I-labelled product bound to each well is determined by gamma detection.

Hybridomas are selected from hybridoma cultures that secrete anti-Pep-1 antibodies into their culture media, and further characterized as described herein.

Hybridomas are produced and selected from hybridoma cultures that secrete anti-Pep-3 antibodies using the methods described above except that polypeptide Pep-3 is used in place of Pep-1 as the immunizing and screening polypeptide.

B. Production and Purification of Pep-1 Monoclonal Antibody

Hybridoma anti-Pep-1 is cultured in a 5% $CO_2$, humidified atmosphere at 37° C. in DMEM containing 2 mM L-glutamine, 50 μg per ml gentamycin, 10% fetal bovine serum, 10% horse serum, all from Grand Island Biological Co., Lawrence, Mass., 10% NCTC medium from Microbiological Associates, Rockville, Md., 1 mM hypoxanthine and 0.3 mM thymidine, both from Sigma Chemical Corp. Cell concentration is kept in the range of about $1-2 \times 10^5$ cells per ml of medium to about $1-2 \times 10^6$ cells per ml of medium for cell growth, division, and production of antibody.

To produce ascites tumor fluid containing anti-Pep-1 antibody molecules, 10-week old Balb/c mice are immunologically primed by intraperitoneal injection with 0.3 ml of mineral oil and subsequently intraperitoneally injected with $3-5 \times 10^5$ anti-Pep-1 hybridoma cells. The inoculated mice are then maintained for a time period sufficient for anti-Pep-1 antibody-containing ascites tumor fluids to accumulate, e.g., for about 10 to about 21 days. The ascites fluid is collected and clarified by centrifugation at 15,000×g for 1 hour at 4° C. and stored frozen at −20° C.

Anti-Pep-1 antibody molecules are isolated from the ascites fluid by subjecting the fluid to fast protein liquid chromatography (FPLC) on a Pharmacia Mono QHR 5/5 anion exchange column in a Pharmacia FPLC System (both from Pharmacia, Inc.) using a 0–0.5M NaCl gradient in 10 mM Tris, pH 8.0, and following the directions supplied with the column. The anti-Pep-1 antibody molecules so isolated can then be transferred to any physiologically tolerable diluent desired by dialysis.

Alternatively, anti-Pep-1 antibody molecules can be isolated from the ascites tumor fluid by precipitation with ammonium sulfate according to the method described by Goding, *Monoclonal Antibodies: Principles and Practice*, Academic Press, p 100–101 (1983). Briefly, that method entails slowly admixing saturated ammonium sulfate to the ascites fluid until about a 45% to about a 50% ammonium sulfate concentration is achieved. The precipitated immunoglobulins are then collected by centrifugation at 2000×g, preferably 10,000×g. The precipitate is washed 2 or 3 times in 40% saturated ammonium sulfate. The precipitated anti-Pep-1 antibody molecules are then dialyzed against 500–1000 volumes of phosphate buffered saline (PBS) or any other physiologically tolerable diluent desired to remove ammonium sulfate. The dialysis fluid is changed several times at intervals of a few hours. The protein concentration of the recovered dialyzed anti-Pep-1 antibody solution is determined by the Lowry method [Lowry et al., *J. Biol. Chem.*, 193, 265–275 (1951)] using a bovine serum albumin standard.

Confirmation of functional anti-Pep-1 antibody specificity in either a serum sample obtained in Example 3 or hybridoma culture supernatant is determined in binding assays to IL-8 receptor-expressing neutrophils in competition assays described below in Example 5.

Hybridoma anti-Pep-3 prepared as described in Example 4A is cultured as described above for hybridoma anti-Pep-1. Anti-Pep-3 antibody molecules are purified from hybridoma anti-Pep-3 as described above for anti-Pep-1 antibody molecules.

Confirmation of functional anti-Pep-3 antibody specificity in either a serum sample obtained in Example 3 or in hybridoma culture supernatant is determined in the Western Blot analysis of Example 3C and in binding assays to IL-8 receptor expressing neutrophils as described in Example 5.

5. Binding and Inhibition of Binding of Iodinated IL-8 to Neutrophils

A. Binding Assays

IL-8, obtained as described in Example 2 was radioiodinated following the Iodogen iodination procedure according to the manufacturer's instructions (Pierce Biochemicals). Separate aliquots of the IL-8 receptor-expressing neutrophils prepared in Example 1 were admixed with increasing concentrations of IL-8 labelled with $^{125}$I as described above. The concentration of the IL-8 in the admixture ranged from $3\times10^{-10}$ to $5\times10^{-9}$M which corresponded to 1000 counts per minute (CPM) up to 110,000 CPM. The admixture was maintained for 20 minutes at room temperature after which time equilibrium was reached. Aliquots of the admixtures were then centrifuged through a mixture of silicon oils at 12,000×g for 5 minutes at room temperature to separate the free IL-8 from the neutrophil-bound IL-8. The total cell-associated radioactivity was determined by gamma counter detection.

Figure 2:
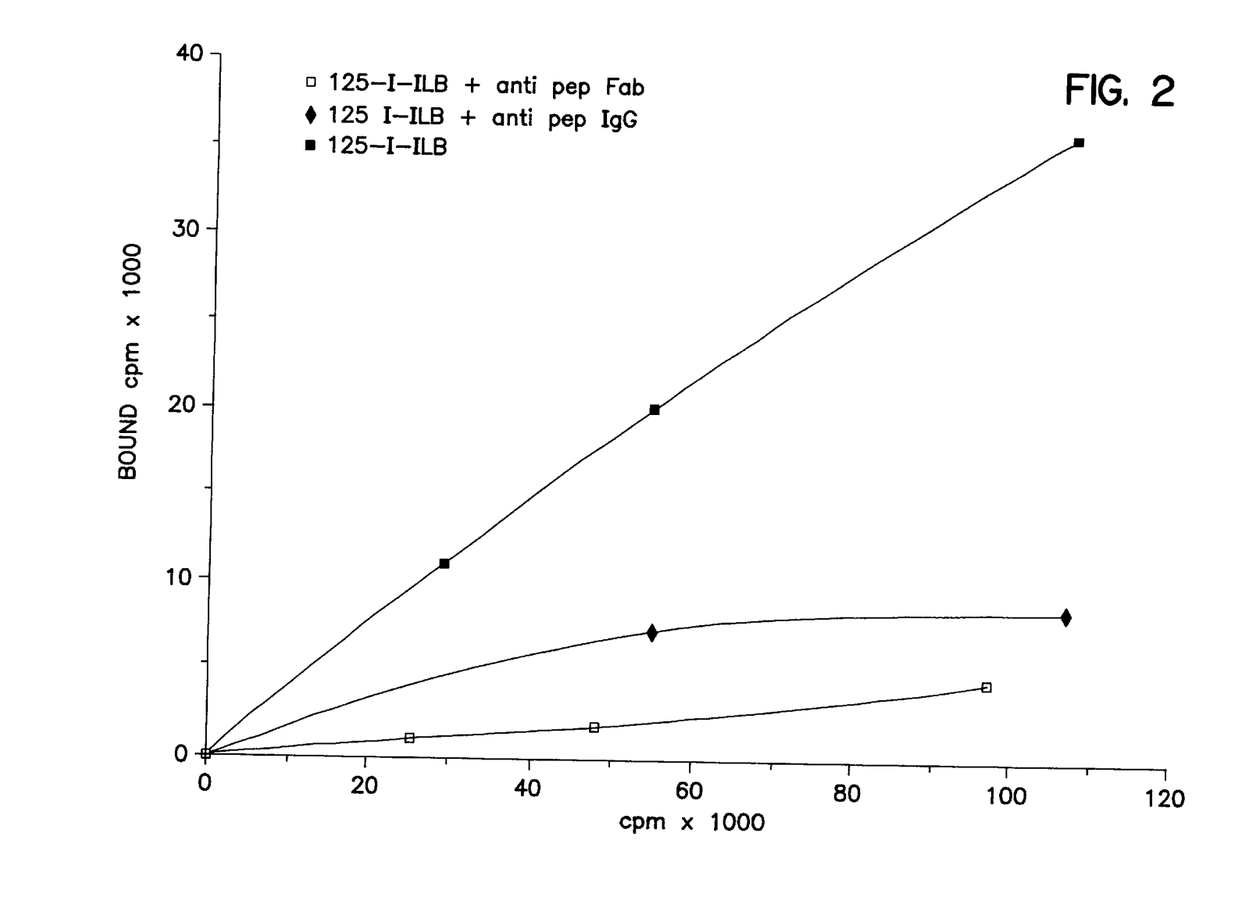
FIG. 2 illustrates the non-saturable binding curve of increasing concentrations of iodinated IL-8 to neutrophils. Specific binding is calculated in the presence of 100-fold molar excess unlabeled IL-8 and is subtracted from the total to calculate the specific binding depicted by the closed squares. Each point is the mean ± standard error of the mean (SEM) of three independent experiments. The binding of IL-8 is inhibited by antibodies directed against the IL-8 related synthetic polypeptide 50–67, Pep-1 (depicted by the closed triangles). FAB fragments of the anti-Pep-1 antibody are more effective than intact antibodies at inhibiting the binding of IL-8 to neutrophils (depicted by the open squares).

Specific cell-associated binding of IL-8 was calculated by subtracting the cell-associated radioactivity that resulted in admixtures maintained in the presence of 100-fold molar excess of unlabelled IL-8 from the total radioactivity. The net or specific results of the binding reaction of iodinated IL-8 to neutrophils is shown in FIG. 2 where each point represents the mean ± the standard error of the mean (SEM) of three independent experiments. The results show that suspensions of IL-8 receptor-bearing neutrophils bound iodinated IL-8 in a specific and non-saturable reaction.

B. Inhibition Assays (1) Anti-Pep-1 Polyclonal Antibodies

The binding of iodinated IL-8 to the IL-8 receptor-interacting site on neutrophils was confirmed by performing inhibition assays with anti-Pep-1 polyclonal antibodies prepared in Example 3. IL-8 was iodinated as described in A. above and increasing concentrations of the labeled IL-8 ranging from $3\times10^{-10}$M up to $1\times10^{-9}$M were separately admixed with 2 mg/ml of anti-Pep-1 polyclonal antibody to form an immunoreaction admixture which was maintained at 37° C. for 30 minutes. FAB fragments of the anti-Pep-1 antibodies were prepared and also evaluated in the inhibition assays following the same procedure. Fab fragments were prepared from sera using manufacturer's protocols and the Immunopure Fab preparation kit (Pierce Chemical Co., Rockford, Ill.).

After the maintenance period, the immunoreaction admixtures were separately admixed to aliquots of $2\times10^6$ neutrophils/ml prepared in Example 1 to form a cellular immunoreaction admixture. The resultant admixture was maintained as performed in the IL-8 binding assays. The binding reaction was terminated as described above.

Specific binding of IL-8 to the IL-8 receptor-interacting site on neutrophils and inhibition of binding by treatment with anti-Pep-1 polyclonal antibodies was calculated as described in A. The binding of IL-8 to the IL-8 receptor-interacting site on neutrophils was inhibited by treatment with either intact anti-Pep-1 antibodies or anti-Pep-1 Fab fragments at all concentrations of iodinated IL-8 evaluated in the assay as shown in FIG. 2. The results indicate that polyclonal antibodies directed against the 50–67 amino acid residue sequence of IL-8, Pep-1, are effective at binding to the active site on IL-8 thereby preventing the binding of IL-8 to the IL-8 ligand-interacting site (receptor) on neutrophils.

(2) Immunoaffinity Purified Anti-Pep-1 and Anti-Pep-3 Polyclonal Antibodies

The ability of anti-IL-8 and immunoaffinity purified antibody compositions prepared in Example 3D to inhibit IL-8 binding to neutrophils bearing IL-8 receptors was also determined. For the inhibition assays, neutrophils were isolated as described in Example 1. The inhibition assays were performed by first admixing separate aliquots of neutrophils at a concentration of $1\times10^7$ cells/ml with 50 µg/ml of Fab fragments of anti-Pep-1 and anti-Pep-3 immunoaffinity purified antibodies to form antibody-cell admixtures. Fab fragments were prepared as described in (1) above.

Anti-IL-8 and a control antibody, anti-11-29 were also tested in this assay. The resultant admixtures were maintained for five minutes at 37° C. prior to admixture of approximately ten µl of $^{125}$I-IL-8 at 40,000 cpm prepared as described in Example 5A. The IL-8-containing admixtures were then maintained for 30 minutes at 37° C. to allow the Il-8 to bind to IL-8 receptors on neutrophils if the receptor-binding site of IL-8 was not blocked by the antibodies tested.

The cells were then centrifuged through a mixture of silicon oils for 15 minutes as described in Example 5A. The radioactivity in the resultant supernatant and the pellet was then measure by gamma detection.

The specific cell-associated binding of IL-8 to neutrophils was calculated as described in Example 5A with the exception that a 200-fold molar excess of unlabelled IL-8 was used to calculate non-specific binding. Percent inhibition was then determined by the calculating the difference between the specific cell-associated binding in the presence compared with in the absence of admixed antibody.

Figure 3:
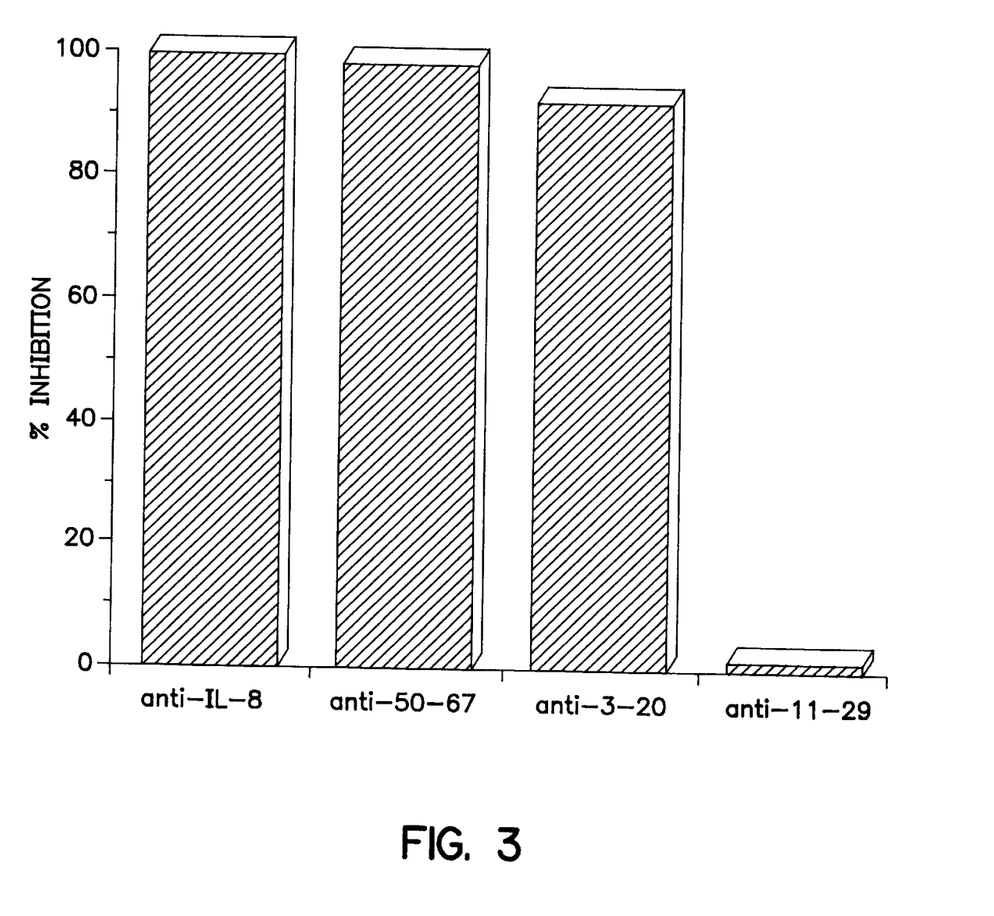
FIG. 3 is a bar graph that illustrates the effects of antibody compositions, anti-IL-8, anti-Pep-1 (anti-50–67), and anti-pep-3 (anti-3–20), immunospecific for polypeptide defined regions of IL-8, on the binding of iodinated IL-8 ($125I$-IL-8) to neutrophils (PMNs) as described in Example 5A(2). The antibody, anti-11-29, served as a control in the experiment as it failed to prevent the inhibition of $^{125}I$-IL-8 binding to PMNs compared to the inhibition seen with the IL-8 specific antibodies.

The results of the inhibition assays are shown in FIG. 3 where both anti-IL-8 and anti-Pep-1 antibodies completely inhibited the binding of iodinated IL-8 to IL-8 receptors on neutrophils. The anti-Pep-3 antibody was nearly 100% effective. No inhibition was seen with the control antibody, 11–29. The results indicated that the immunoaffinity purified polyclonal antibodies, Pep-1 and Pep-3, directed against the 50–67 amino acid residue sequence and the 3–20 amino acid residue sequence, respectively, of IL-8 were both effective at binding to the active site on IL-8 thereby preventing the binding of IL-8 to the IL-8 receptors on neutrophils.

(3) Anti-Pep-1 Monoclonal Antibodies

Purified anti-Pep-1 monoclonal antibodies prepared in Example 4 are also evaluated as competitive inhibitors of $^{125}$I-IL-8 binding to the IL-8 receptor-interacting site on neutrophils in assays performed as described for polyclonal antibodies.

6. Inhibition of Neutrophil Activation with IL-8 Related Synthetic Polypeptide Antibodies A. Anti-Pep-1 Polyclonal Antibodies Anti-Pep-1 polyclonal antibodies prepared in Example 3 were evaluated for their ability to inhibit neutrophil activation measured by calcium mobilization as performed in Example 2.A.(2). Pep-1, prepared in Example 1., was admixed with anti-Pep-1 polyclonal antibodies to form a peptide immunoreaction admixture as described in Example 5A. An aliquot of isolated IL-8 receptor-expressing neutrophils prepared in Example 1 was admixed with the Pep-1/anti-Pep-1 admixture and was maintained as performed in Example 2A(2). The admixture was subjected to fluorometry for measurement of calcium mobilization as performed in Example 2A(2).

Anti-Pep-1 polyclonal antibodies inhibited the calcium mobilization induced by Pep-1 as shown in FIG. 1. The results indicate that polyclonal antibodies directed against the 50–67 amino acid residue sequence of IL-8, Pep-1, are effective at binding to the active site on IL-8 thereby preventing the binding of IL-8 to the IL-8 receptor-interacting site on neutrophils and preventing the consequent neutrophil activation measured by calcium mobilization.

B. Anti-Pep-1 Monoclonal Antibodies

Purified anti-Pep-1 monoclonal antibodies prepared in Example 4 are also evaluated for their ability to inhibit neutrophil activation in calcium mobilization assays. The assays are performed as described for polyclonal antibodies in A above.

Although the present invention has now been described in terms of certain preferred embodiments, and exemplified with respect thereto, one skilled in the art will readily appreciate that various modifications, changes, omissions and substitutions may be made without departing from the spirit thereof. It is intended, therefore, that the present invention be limited solely by the scope of the following claims.

What is claimed is:

1. A polyclonal antibody immunoaffinity purified against a region of interleukin-8 (IL-8) having an amino acid residue sequence selected from the group consisting of:

LysGluLeuArgCysGln-CysIleLysThrTyrSerLysProPheHisProLys and

CysLeuAspProLysGluAsnTrpVal-GlnArgValValGluLysPheLeuLys.

2. The polyclonal antibody of claim 1 wherein the region has the amino acid residue sequence LysGluLeuArgCysGln-CysIleLysThrTyrSerLysProPheHisProLys.

3. The polyclonal antibody of claim 1 wherein the region has the amino acid residue sequence CysLeuAspProLysGluAsnTrpVal-GlnArgValValGluLysPheLeuLys.

4. A monoclonal antibody that immunoreacts with a region of interleukin-8 (IL-8) having an amino acid residue sequence selected from the group consisting of:

LysGluLeuArgCysGln-CysIleLysThrTyrSerLysProPheHisProLys and

CysLeuAspProLysGluAsnTrpVal-GlnArgValValGluLysPheLeuLys.

5. The monoclonal antibody of claim 4 wherein the region has the amino acid residue sequence LysGluLeuArgCysGln-CysIleLysThrTyrSerLysProPheHisProLys.

6. The monoclonal antibody of claim 4 wherein the region has the amino acid residue sequence CysLeuAspProLysGluAsnTrpVal-GlnArgValValGluLysPheLeuLys.

* * * * *